United States Patent [19]

Waldmann et al.

[11] 4,013,709
[45] Mar. 22, 1977

[54] PRODUCTION OF ω-FORMYL CARBOXYLIC ACID ESTERS

[75] Inventors: Helmut Waldmann, Leverkusen; Wulf Schwerdtel, Leverkusen-Steinbuechel; Wolfgang Swodenk, Odenthal-Gloebusch, all of Germany

[73] Assignee: Bayer Aktiengesellschaft, Leverkusen, Germany

[22] Filed: Jan. 23, 1976

[21] Appl. No.: 651,989

Related U.S. Application Data

[62] Division of Ser. No. 410,074, Oct. 26, 1973.

[30] Foreign Application Priority Data

Oct. 27, 1972 Germany .............. 2252780

[52] U.S. Cl. .................. 260/483; 260/404; 260/404.5; 260/408; 260/410.5; 260/410.9 R; 260/465 D; 260/465.4; 260/468 J; 260/468 K; 260/473 R; 260/476 R; 260/479 S

[51] Int. Cl.² .................................. C07C 67/00

[58] Field of Search ........... 260/483, 468 J, 465 D, 260/465.4, 476 R, 473 R, 479 S, 410.5, 410.9 R, 408, 404, 404.5, 468 K

[56] References Cited

OTHER PUBLICATIONS

J.A.C.S., 64(1942), p. 1419.
J. Org. Chem. 12, (1947), p. 163.

Primary Examiner—Vivian Garner
Attorney, Agent, or Firm—Burgess, Dinklage & Sprung

[57] ABSTRACT

A process for the production of an ω-formyl carboxylic acid ester, comprising reacting an enol ether of a cyclic ketone with hydrogen peroxide in the presence of at least one catalyst selected from the group consisting of a compound of boron or of a metal of the Fifth or Sixth Secondary Group of the Periodic Table. Advantageously the enol ether has the formula

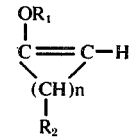
(I)

wherein
$R_1$ is alkyl of 1 to about 3 carbon atoms, cycloalkyl of 5 or 6 carbon atoms or phenyl optionally substituted by fluorine, chlorine, alkoxy of 1 to about 3 carbon atoms, cyano or phenyl,
$n$ is an integer of about 3 to 10, and
$R_2$ each independently is hydrogen, fluorine, chlorine, cyano, alkoxy of 1 to about 4 carbon atoms, alkyl of 1 to about 6 carbon atoms, cycloalkyl of 5 to 7 carbon atoms or phenyl optionally substituted by fluorine, chlorine, cyano, alkoxy of 1 to about 4 carbon atoms or alkyl of 1 to about 6 carbon atoms, and the catalyst comprises about 15 to 25 mole % based on the hydrogen peroxide of a boron oxide, a boric acid, a salt of a boric acid, a boron halogen compound, a complex boron compound or a boric acid ester of the formula

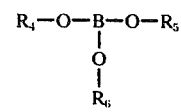
(III)

wherein
$R_4$, $R_5$ and $R_6$ each independently is alkyl of 1 to about 6 carbon atoms optionally substituted by hydroxyl, fluorine, chlorine, alkoxy of 1 to about 3 carbon atoms or phenyl, cycloalkyl of 5 to 7 carbon atoms or phenyl optionally substituted by fluorine, chlorine or alkyl of 1 to about 3 carbon atoms, or about 0.01 to 1 mole % of at least one acetate, benzoate, acetylacetonate or naphthenate of a metal of the Fifth or Sixth Group of the Periodic table.

9 Claims, No Drawings

PRODUCTION OF ω-FORMYL CARBOXYLIC ACID ESTERS

This is a division of application Ser. No. 410,074, filed Oct. 26, 1973, now pending.

This invention relates to a process for the production of ω-formyl carboxylic acid esters by reacting enol ethers of cyclic ketones with hydrogen peroxide, optionally in the presence of another epoxidizing agent.

ω-formyl carboxylic acid esters represent valuable intermediate products for the synthesis of medicaments and they can also be used in the form of their acetals as flotation agents.

It is known that certain ω-formyl carboxylic acid esters can be obtained from α, ω-dicarboxylic acid derivatives by reduction with palladium (J. Org. Chem. 12, (1947) 163) or by splitting 2-hydroxy-1-cyclohexanone for example with lead tetraacetate in the presence of ethanol (J. Am. Soc. 64, 1419 (1942). Both these processes are complicated and only have limited selectivity in regard to the resulting ω-formyl carboxylic acid esters.

We have now found that ω-formyl carboxylic acid esters can be obtained by reacting enol ethers of cyclic ketones with hydrogen peroxide in the presence of a compound of boron or of a compound of a metal of the Fifth or Sixth Secondary Group or of a mixture of a compound of boron with a compound of a metal of the Fifth or Sixth Secondary Group, optionally in the presence of another epoxidizing agent.

Enol ethers of cyclic ketones suitable for use in the process according to the invention are compounds which correspond to the general formula

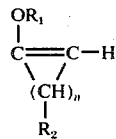

wherein
$R_1$ is alkyl of 1 to about 3 carbon atoms, cycloalkyl of 5 or 6 carbon atoms or phenyl optionally substituted by fluorine, chlorine, alkoxy of 1 to about 3 carbon atoms, cyano or phenyl,
$n$ is an integer of about 3 to 10, and $R_2$ each independently is hydrogen, fluorine, chlorine, cyano, alkoxy of 1 to about 4 carbon atoms, alkyl of 1 to about 6 carbon atoms, cycloalkyl of 5 to 7 carbon atoms or phenyl optionally substituted by fluorine, chlorine, cyano, alkoxy of 1 to about 4 carbon atoms or alkyl of 1 to about 6 carbon atoms.

Particularly suitable are compounds of the general formula

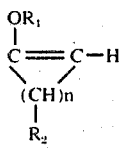

wherein
$R_1$ is alkyl of 1 to about 3 carbon atoms optionally substituted by fluorine, chlorine, alkoxy of 1 to about 3 carbon atoms or cyano, and $n$ is 3, 4 or 5.

The following are mentioned as examples for $R_1$: methyl, monofluoromethyl, monochloromethyl, ethyl, β-monofluoroethyl, β-monochloroethyl, β-cyanoethyl, β-methoxyethyl, β-ethoxyethyl, n-propyl, γ-methoxypropyl, γ-cyanopropyl, isopropyl, β-methoxyisopropyl and β-chloroisopropyl.

The following individual compounds are mentioned by way of example: 1-methoxycyclopentene, 1-methoxy-3-fluorocyclopentene, 1-ethoxycyclopentene, 1-ethoxy-4-ethoxycyclopentene, 1-ethoxy-5-cyanocyclopentene, 1-isopropoxycyclopentene, 1-ispropoxy-4-phenylcyclopentene, 1-methoxy-4-isopropoxycyclohexene, 1-(monofluoromethoxy)-cyclohexene, 1-(cyclohexyloxy)-cyclohexene,1-(phenyloxy)-cyclohexene, 1-(β-cyanoethyloxy)-cyclohexene, 1-ethyloxycyclohexene 1-n-propoxycyclohexane, 1-isopropoxycyclohexene, 1-methoxycycloheptene, 1-ethoxycycloheptene, 1-ethoxy-4-5-dimethyl cycloheptene, 1-methoxycyclooctene, 1-ethoxycyclooctene, 1-ethoxycyclododecene, 1-methoxycyclododecene, and the like.

In the process according to the invention, it is possible to add either a compound of a metal of the Fifth and Sixth Secondary Group or a compound of boron and also mixtures of a compound of boron with a compound of a metal of the Fifth or Sixth Secondary Group. In the case of compounds of the metals of the Fifth and Sixth Secondary Group, it is particularly preferred to use compounds of these metals with organic acids, for example acetates, benzoates, naphthenates and acetyl acetonates. In addition, it is also possible to use compounds of the metals of the Fifth and Sixth Secondary Group such as carbonyls, nitrosocarbonyls or carbonylates. Compounds of vanadium and molybdenum are particularly suitable. The following are mentioned by way of example: molybdenum hexacarbonyl, vanadium-(II)-acetate, vanadium-(II)-acetylacetonate, vanadium-(II)-benzoate, vanadium-(II)-naphthenate, vanadium-(III)-acetate, vanadium-(III)-acetylacetonate, vanadium-(III)-benzoate, vanadium-(III)-naphthenate, vanadylacetylacetonate, vanadylnaphthenate, niobium acetate, chromium-(II)-acetate, chromium-(II)-acetylacetonate, chromium-(III)-acetate, chromium-(III)-acetylacetonate, chromium-(III)-naphthenate, molybdenum-(II)-acetylacetonate, molybdenum-(II)-acetate, molybdenum-(II)-benzoate, molybdenum-(III)-acetylacetonate, molybdenum-(III)-acetate, molybdenum-(III)-benzoate, molybdenum-naphthenates, molybdenylacetylacetonates, tungsten-(III)-acetate and tungstylacetonate.

Suitable boron compounds include boron oxides, boric acids, salts and esters of boric acids, boron-halogen compounds, boron phosphates and complex boron compounds.

The following are mentioned as examples of boric acids: orthoboric acid, metaboric acid and tetraboric acid. Suitable salts include the alkali and alkaline earth salts of these acids, also their zinc and aluminum salts. The following are mentioned by way of example: sodium orthoborate, sodium metaborate, sodium tetraborate, lithium orthoborate, lithium metaborate, lithium tetraborate, potassium orthoborate potassium metaborate, potassium tetraborate, magnesium orthoborate, magnesium metaborate, magnesium tetraborate, calcium orthoborate, calcium metaborate, calcium tetraborate, zinc orthoborate, zinc metaborate, zinc tetraborate, aluminum orthoborate, aluminum metaborate and aluminum tetraborate.

Suitable boric acid esters are compounds corresponding to the general formula

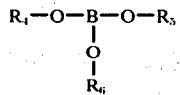

III wherein $R_4$, $R_5$ and $R_6$ each independently is alkyl of 1 to about 6 carbon atoms optionally substituted by hydroxyl, fluorine, chlorine, alkoxy of 1 to about 3 carbon atoms or phenyl, cycloalkyl of 5 to 7 carbon atoms of phenyl optionally substituted by fluorine, chlorine or alkyl of 1 to about 3 carbon atoms.

The following are mentioned as examples of $R_4$, $R_5$ and $R_6$: chloromethyl, hydroxymethyl, $\beta$-hydroxymethyl, $\beta$-methoxyethyl, 3-propoxypropyl, toluene, ethylphenyl, propylphenyl and tert.-butylphenyl.

The following boric acid esters are mentioned by way of example: boric acid trimethyl ester, boric acid triethyl ester, boric acid tri-n-hexylester, boric acid tricyclohexyl ester, boric acid tri-($\beta$-methoxyethyl)-ester, boric acid tri-($\beta$-fluoroethyl)-ester, boric acid triphenyl ester, boric acid tri-(p-chlorophenyl)-ester, boric acid tri-(p-methoxy phenyl)-ester, boric acid tri-($\beta$-hydroxyethyl)-ester, and the like.

Boron trifluoride and boron trichloride are mentioned as examples of halogen compounds of boron. Suitable complex boron compounds are compounds which represent adducts of alcohols corresponding to the general formula $R_4$—OH, of alcoholates corresponding to the general formula $R_4$—OMe, of ethers corresponding to the general formula $R_4$—O—$R_5$, of carboxylic acids corresponding to the general formula $R_4$—COOH or of hydrogen halide, with compounds of general formula III, borontrifluoride $R_4$ and $R_5$ having the same meaning as in general formula III, while Me in the case of the alcoholates represents the alkali or alkaline earth metals, zinc or aluminum. The following are mentioned by way of example: tetramethoxyboric acid, lithium tetramethoxyborate, sodium tetramethoxyborate, magnesium ditetramethoxyborate, zinc ditetramethoxyborate, boron trifluoride diethyletherate, borontrifluoride trimethyl etherate, borontrifluoride acetic acid, borontrifluoride propionic acid, tetrafluoroboric acid and sodium trimethoxy monocyclohexyloxyborate.

Boric acid anhydride can also be used. The quantity in which the added compound of metals of the Fifth and Sixth Secondary Group is used can fluctuate within wide limits. However, it is sufficient to use small quantities. In general, quantities of less than about 10 mole %, based on the quantity of hydrogen peroxide used, are employed. It is preferred to use quantities of about 0.01 to 1 mole % based on the quantity of hydrogen peroxide used. The added compound can be either soluble or insoluble in the reaction mixture. The compounds can also be applied to inert supports, for example aluminum oxide, aluminum oxide hydrate, silica gel or zeolites, and used in this form.

In cases where boron compounds are added, they are generally employed in quantities of about 3 to 30 mole %, based on the quantity of hydrogen peroxide, quantities of about 15 to 25 mole % being preferred.

The quantitative ratio of boron compound to the compound of a metal of the Fifth or Sixth Secondary Group in the mixtures added is by no means critical. In general, the boron compound used will generally be employed in a larger quantity (mole %) than the other compounds, based on the quantity of hydrogen peroxide used. It is particularly preferred to use mixtures of molybdenum-(III)-acetylacetonate and boric acid anhydride, molybdenum-(III)-acetylacetonate and boric acid trimethylester.

It is preferred to use non-aqueous solutions of hydrogen peroxide in the process according to the invention. Non-aqueous solutions of hydrogen peroxide such as these are known per se and are obtained for example in accordance with German DAS No. 1,802,103. In addition, non-aqueous hydrogen peroxide solutions of this kind can be obtained by adding a solvent miscible with water and hydrogen peroxide to the aqueous hydrogen peroxide solutions and subsequently removing the water, preferably by vacuum distillation. Solvents suitable for this purpose include esters, N-alkyl-substituted acid amides, alcohols, carboxylic acids, sulfonic acids and phosphoric acids. The esters and alkylamides of phosphoric acids, phosphonic acids and phosphinic acids are particularly suitable, the following being mentioned as examples: triethyl phosphate methane phosphonic acid dimethyl ester, $\beta$-cyanoethyl phosphonic acid dimethyl ester, $\beta$-carbomethoxy phosphonic acid methyl ester, trioctyl phosphate, trihexyl phosphate, butyl acetate, isoamyl acetate and cyclohexyl acetate.

It is also possible to use solvent mixtures which afford advantages over the use of a single solvent in regard to the simultaneous dissolution of hydrogen peroxide, the added compound, the enol ether and the $\omega$-formyl carboxylic acid ester formed. Thus, it is advantageous, for example, to start with a fairly highly concentrated parent solution of hydrogen peroxide in a phosphonic acid ester of phosphoric acid ester, such as a 30% solution of hydrogen peroxide in methane phosphonic acid dimethylester, and to add to this solution an inert solvent, such as ethylacetate, butylacetate or methylene chloride, so that the solubility of the added compound and the enol ether used is increased.

The concentration of the non-aqueous hydrogen peroxide solutions used can fluctuate within wide limits and in practice is determined solely by the explosion limits. Accordingly, the upper limit to the concentration of hydrogen peroxide in non-aqueous hydrogen peroxide solutions is from 30 to 60%, depending on the solvent used. In general, hydrogen peroxide is used in concentrations of about 3 to 30% based on the quantity of hydrogen peroxide used. It is preferred to use non-aqueous solutions of hydrogen peroxide with a concentration of about 10 to 20%.

In addition to hydrogen peroxide, organic and inorganic peracids, peroxides and hypochlorites can be used as epoxidizing agents. The use of these compounds as epoxidizing agents is known per se.

Preferred peracids include linear and branched organic peracids containing up to about 10 carbon atoms, organic peracids containing about 2 to 4 carbon atoms being preferred. The following are mentioned by way of example: performic acid peracetic acid, perpropionic acid, perisobutyric acid, perbenzoic acid and monoperoxyphthalic acid.

Linear or branched alkyl peroxides with up to about 16 carbon atoms are used as the peroxides, those with alkyl radicals of about 4 to 12 carbon atoms being preferred. It is also possible to use aromatic peroxides. The following peroxides are mentioned by way of example: tert.butyl hydroperoxide, ethylbenzene hydroperoxide, cumene hydroperoxide and anthraquinone hydroperoxide.

Alkyl peroxides of this kind are always used in conjunction with catalysts such as compounds of molybdenum and vanadium that are soluble in organic solvents, for example in conjunction with molybdenum naphthenate, molybdenum acetylacetonate or vanadium acetylacetonate. Silica gel, optionally activated with titanium or boron compounds, can also be used as the epoxidizing agent.

The process according to the invention is generally carried out by initially introducing into the reactor the enol ether of a cyclic ketone, optionally together with an epoxidizing agent, subsequently adding hydrogen peroxide together with a compound of boron or a compound of a metal of the Fifth or Sixth Secondary Group or a mixture of a boron compound with a compound of a metal of the Fifth or Sixth Secondary Group, or by initially introducing hydrogen peroxide together with a compound of boron or a compound of a metal of the Fifth or Sixth Secondary Group or a mixture of a boron compound with a compound of a metal of the Fifth or Sixth Secondary Group, optionally together with the epoxidizing agent, and subsequently adding the enol ether of a cyclic ketone.

The temperature at which the process according to the invention is carried out is generally in the range from −80° to +30° C., temperatures of about −20° C. to +20° C. being preferred.

The reaction time is largely determined by the particular type of enol ether used. As a rule, it amounts to between about 30 minutes and 4 hours.

The pressure at which the process according to the invention is carried out is determined by the vapor pressure of the reactants and of the particular solvent used. It does not have any critical effect upon the process according to the invention. The process according to the invention can be carried out both in the liquid phase and in the gaseous phase.

The reaction mixture is worked up by methods known per se. In general, it is best to remove the metal or boron compounds added in known manner, for example by adding acetates or carbonates of the alkali metals. They can also be removed by absorption on aluminum oxide or silica gel.

The ω-formyl carboxylic acid esters are isolated by methods known per se, for example by distillation, extraction or crystallization.

EXAMPLE 1

58.2 g of a 9.3% solution of peracetic acid in n-butyl acetate were added dropwise with stirring at 0° C to a mixture of 8.4 g of 1-methoxy cyclohexene, 30.4 g of an 8.38 % solution of hydrogen peroxide in triisooctylphosphate and 0.3 g of molybdenum-(III)-acetylacetonate, and stirring was continued for another 2 hours. Analysis of the reaction mixture at this point revealed a content of 1.8% of 2-hydroxy cyclohexanone and 6.2% of ω-formyl valeric acid methyl ester. The reaction mixture was worked up by centrifuging off the insoluble constituents, adding 15 ml of a 10% aqueous sodium hydroxide solution at 0° to −10° C, centrifuging the mixture again and waiting for the phases to separate. The upper phase obtained was washed with saturated sodium chloride solution, dried over anhydrous magnesium sulfate, filtered and the butyl acetate present distilled off at 15 mmHg through a small glass column.

According to analysis by gas chromatography, the residue of 35.4 g contained 16.5 % of ω-formyl valeric acid ester. Fractionation under vacuum in a microcolumn at a pressure of 11 mm Hg gave first runnings at 76°–85° C of 1.6g of 2-hydroxy cyclohexanone. 5.0 g of ω-formyl valeric acid methyl ester distilled over as the main fraction at 107°–112° C.

The 2-hydroxy cyclohexanone and ω-formyl valeric acid methyl ester were identified as follows:

a. 2-hydroxy cyclohexanone m.p. 127° C molecular weight according to analysis by mass spectrometry: 114

| Elemental analysis: | % C | % H | % O |
|---|---|---|---|
| found: | 63.2 | 9.1 | 28.3 |
| calculated: | 63.2 | 8.8 | 28.1 |

The infra-red spectrum corresponds to that of the authentic compound.

b. ω-formyl valeric acid methyl ester B.P.$_{11}$: 110° C

The NMR-spectrum corresponds to the sructure of the ω-formyl valeric acid methyl ester.

The infra-red spectrum does not show any OH-absorption but strong absorptions at 17.25 cm$^{-1}$ (aldehyde carbonyl) and at 17.45 cm$^{-1}$ (ester carbonyl).

| Elemental analysis: | % C | % H |
|---|---|---|
| found: | 58.4 | 7.7 |
| calculated: | 58.5 | 7.3 |

EXAMPLE 2

58.2 g of a 9.3% peracetic acid solution in n-butyl acetate were gradually added with stirring at 10° C to 8.4 g of 1-methoxy cyclohexene. On completion of the addition stirring was continued for another 20 minutes, a solution of 2.5 g of hydrogen peroxide and 0.3 of molybdenum-(III)-acetylacetonate in 17.5 g of triisooctylphosphate were added dropwise at −10° C and stirring was continued for another 2.5 hours. Analysis by gas chromatography at this stage showed that the reaction mixture contained 5.95% of ω-formyl valeric acid ester.

The reaction product can be worked up in accordance with Example 1.

EXAMPLE 3

58.2 g of a 9.3 % solution of peracetic acid in n-butyl acetate were added with stirring at −10° C to 8.4 g of 1-methoxy cyclohexene. Stirring was then continued for another 20 minutes, after which 2.5 g of hydrogen peroxide and 0.1 g of boron trifluoride diethyletherate in 17.5 g of triisooctyl phosphate were added at −10° C, followed by stirring for another 3 hours. Analysis of the reaction mixture by gas chromatography at this stage showed that it contained 4.4% of ω-formyl valeric acid methyl ester.

EXAMPLE 4

58.2 g of a 9.3% solution of peracetic acid in n-butyl acetate were added dropwise at −10° C to 8.4 g of 1-methoxy cyclohexane, followed by stirring for another 20 minutes.

A solution of 2.5 g of hydrogen peroxide, 0.3 g of molybdenum-(III)-acetylacetonate in 87.5 g of isoamyl acetate was then added at −10° C, followed by stirring for another 4 hours. Analysis by gas chromatography at this stage showed that the reaction mixture contained 1.2 % of 2-hydroxy cyclohexanone and 4.7% of ω-formyl valeric acid methyl ester.

EXAMPLE 5

58.2 g of a 9.3% peracetic solution in n-butyl acetate were gradually added with stirring at −10° C to 8.4 g of 1-methoxy cyclohexene. On completion of the addition, stirring was continued for another 20 minutes, after which 0.3 g of molybdenum-(III)-acetylacetonate and 1.0 g of boric acid trimetyl ester were added, followed by the dropwise addition of 2.5 g of hydrogen peroxide in 17 g of triisooctyl phosphate. Stirring was then continued for another 2.5 hours. Analysis of the reaction mixture by gas chromatography at this stage showed that it contained 6.2% of ω-formyl valeric acid ester.

Other enol ethers which may be similarly reacted include:

1-p-isopropoxyphenoxy-3-n-butyl-cyclohexene, 1-cyclohexyloxy-3,5-diphenyl-cyclohexene, 1-isopropoxy-3-chloro-4-ethoxy-cyclooctene, 1-p-cyanophenoxy-3-fluoro-4-butyl-cyclohexene, 1-p-chlorophenoxy-3-cyano-4-tolyl-cyclohexene, 1-methoxy-3-cyclohexyl-4-p-cyanophenyl-cycloheptene, and the like.

It will be appreciated that the instant specification and examples are set forth by way of illustration and not limitation, and that various modifications and changes may be made without departing from the spirit and scope of the present invention.

What is claimed is:

1. A process for the production of an ω-formyl carboxylic acid ester, comprising reacting hydrogen peroxide with an enol ether of a cyclic ketone of the formula

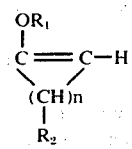

wherein
$R_1$ is alkyl of 1 to 3 carbon atoms, or alkyl of 1 to 3 carbon atoms substituted by fluorine, chlorine, alkoxy of 1 to 3 carbon atoms, cyano or phenyl, $n$ is an integer of about 3 to 10, and $R_2$ each independently is hydrogen, fluorine, chlorine, cyano, alkoxy of 1 to 4 carbon atoms, alkyl of 1 to 6 carbon atoms, alkyl of 1 to 6 carbon atoms substituted by fluorine, chlorine, cyano or alkoxy of 1 to 4 carbon atoms, alkoxy of 1 to 4 carbon atoms substituted by fluorine, chlorine, cyano, alkoxy of 1 to 4 carbon atoms or alkyl of 1 to 6 carbon atoms, in the presence of a catalyst consisting essentially of a carboxylate, carbonyl, nitrosocarbonyl, acetonate or acetylacetonate of a metal of the Fifth or Sixth Secondary Group of the Periodic Table at a temperature of −80° to +30° C.

2. A process as claimed in claim 1, wherein $R_1$ is alkyl of 1 to 3 carbon atoms or alkyl of 1 to 3 carbon atoms substituted by fluorine, chlorine, alkoxy of 1 to 3 carbon atoms or cyano.

3. A process as claimed in claim 2, wherein $n$ is 3, 4 or 5.

4. A process as claimed in claim 1, wherein the enol ether is 1-methoxy cyclohexene.

5. A process as claimed in claim 1, wherein the catalyst consists essentially of at least one acetate, benzoate, acetylacetonate or naphthenate of a metal of the Fifth or Sixth Secondary Group of the Periodic Table.

6. A process as claimed in claim 5, wherein the catalyst consists essentially of at least one acetate, benzoate, acetylacetonate or naphthenate of vanadium or molybdenum.

7. A process as claimed in claim 6, wherein the catalyst is molybdenum-(III)-acetylacetonate.

8. A process as claimed in claim 1, wherein the hydrogen peroxide is used dissolved in a non-aqueous solvent selected from the group consisting of an alcohol, a carboxylic acid, an ester, an acid amide and a fluorine- or chlorine- substituted hydrocarbon, or an ester or an alkylamide of a phosphoric acid, phosphonic acid or phosphinic acid.

9. A process as claimed in claim 8, wherein the solvent is tributylphosphate, trioctylphosphate or isoamyl acetate.

* * * * *